United States Patent
Obando

(10) Patent No.: US 9,421,120 B2
(45) Date of Patent: Aug. 23, 2016

(54) VERTICAL AND HORIZONTAL NASAL SPLINTS AND METHODS OF USE

(76) Inventor: Marcelo Obando, Honolulu, HI (US)

( * ) Notice: Subject to any disclaimer, the term of this patent is extended or adjusted under 35 U.S.C. 154(b) by 1115 days.

(21) Appl. No.: 12/608,701

(22) Filed: Oct. 29, 2009

(65) Prior Publication Data

US 2011/0106140 A1  May 5, 2011

(51) Int. Cl.
*A61F 5/08* (2006.01)
(52) U.S. Cl.
CPC .......................................... *A61F 5/08* (2013.01)
(58) Field of Classification Search
CPC ....................................................... A61F 5/08
USPC ........ 606/199, 201, 196, 204.45; 128/200.24, 128/858, 848; 602/902, 5
See application file for complete search history.

(56) References Cited

U.S. PATENT DOCUMENTS

| | | | | |
|---|---|---|---|---|
| 5,022,389 | A * | 6/1991 | Brennan | 606/204.45 |
| 5,669,377 | A * | 9/1997 | Fenn | 128/200.24 |
| 5,769,089 | A * | 6/1998 | Hand et al. | 128/858 |
| 5,961,537 | A * | 10/1999 | Gould | A61F 5/08 606/204.45 |
| 5,976,173 | A * | 11/1999 | Berke | 606/204.45 |
| 6,453,901 | B1 * | 9/2002 | Ierulli | 128/200.24 |
| 6,663,649 | B2 * | 12/2003 | Stratton | 606/199 |
| 7,114,495 | B2 | 10/2006 | Lockwood, Jr. | |
| 2003/0187374 | A1 * | 10/2003 | Nishioka | 602/5 |
| 2005/0187502 | A1 * | 8/2005 | Krempel et al. | 602/5 |
| 2007/0255309 | A1 * | 11/2007 | Guyuron et al. | 606/199 |
| 2008/0184995 | A1 | 8/2008 | Ierulli | |
| 2008/0257341 | A1 | 10/2008 | Ierulli | |
| 2009/0020115 | A1 | 1/2009 | Lockwood, Jr. | |

* cited by examiner

*Primary Examiner* — Richard Louis
(74) *Attorney, Agent, or Firm* — Greenberg Traurig, LLP

(57) ABSTRACT

A nasal opening device. The nasal opening device includes a vertical splint configured to extend from an upper portion of a nose to a lower level of nasal bones and a horizontal splint configured to extend from a first lateral wall to a second lateral wall of a nose. A vertical flexible member is integrated with said vertical splint and positioned such that upon attachment of the vertical splint to a nose the flexible member is adjacent to a nose tip and assists with maintaining a nose tip in an elevated position, said vertical splint having an adhesive layer for attachment to a nose. A flexible member is integrated with said horizontal splint and extends from said first lateral wall to said second lateral wall of a nose.

17 Claims, 7 Drawing Sheets

VERTICAL AND HORIZONTAL NASAL SPLINTS AND METHODS OF USE

FIELD OF THE INVENTION

The embodiments of the present invention relate to a nasal splint system utilizing both vertical and horizontal splints to open the nasal passage of a wearer.

BACKGROUND

Nasal splints have become ubiquitous in the marketplace. Numerous companies make and sell over-the-counter nasal splints designed to improve the intake of oxygen. In one instance, the nasal splints are marketed as a remedy to snoring. In other instances, athletes wear the nasal splints during strenuous activities such as games to increase oxygen intake and therefore stamina and performance. While both horizontal and vertical nasal splints have been marketed, the marketed versions suffer from drawbacks. Primarily, the marketed nasal splints are generally not as effective as needed and tend to disengage from a nose to which they are attached.

Thus, there is a need for more effective system of nasal splints which stay attached during strenuous activities.

SUMMARY

Accordingly, the embodiments of the present invention comprise a nasal splint having a horizontal and vertical component. The horizontal component expands the connective tissue laterally and the external area of the nasal valves generally. The vertical component elevates the nasal columella and the nasal tip. In this manner, the width of the lumens of the lower portion of the nose are increased significantly to improve oxygen intake.

In one embodiment, the horizontal splint includes a center strip extending to oppositely positioned triangular ends which, when the horizontal splint is worn, attach to the outer sides of the wearer's nose. In one embodiment, the vertical splint extends from an upper portion of the nose to the lip portion below the nose. The horizontal and vertical splints may be individual components or a single component.

Other variations, embodiments and features of the present invention will become evident from the following detailed description, drawings and claims.

DETAILED DESCRIPTION

Figure 1:
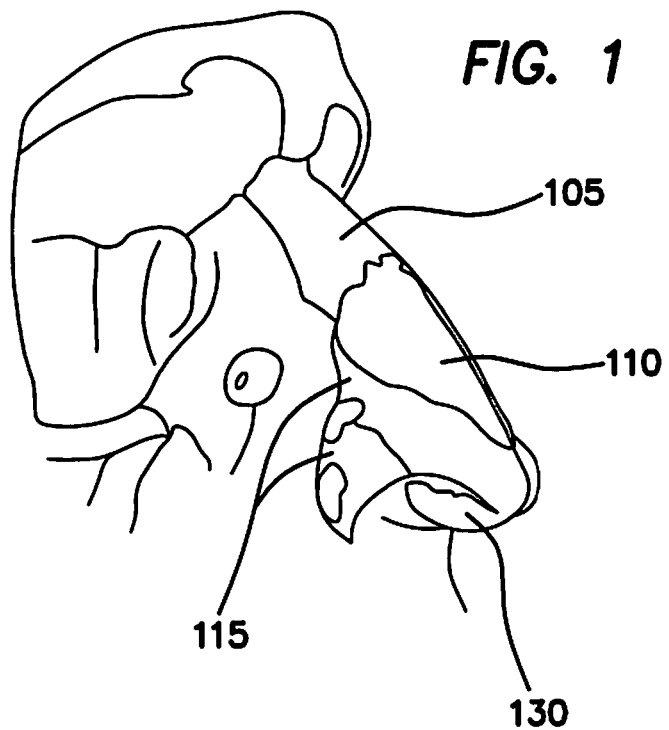
FIG. 1 illustrates a side view of the skeletal anatomy of the human nose.

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed.

The embodiments of the present invention relate to nasal splints configured to improve the oxygen intake via a wearer's nose. The increase in oxygen provides extended stamina during strenuous activities and may also reduce or eliminate episodes of snoring and sleep apnea during periods of sleep.

Figure 2:
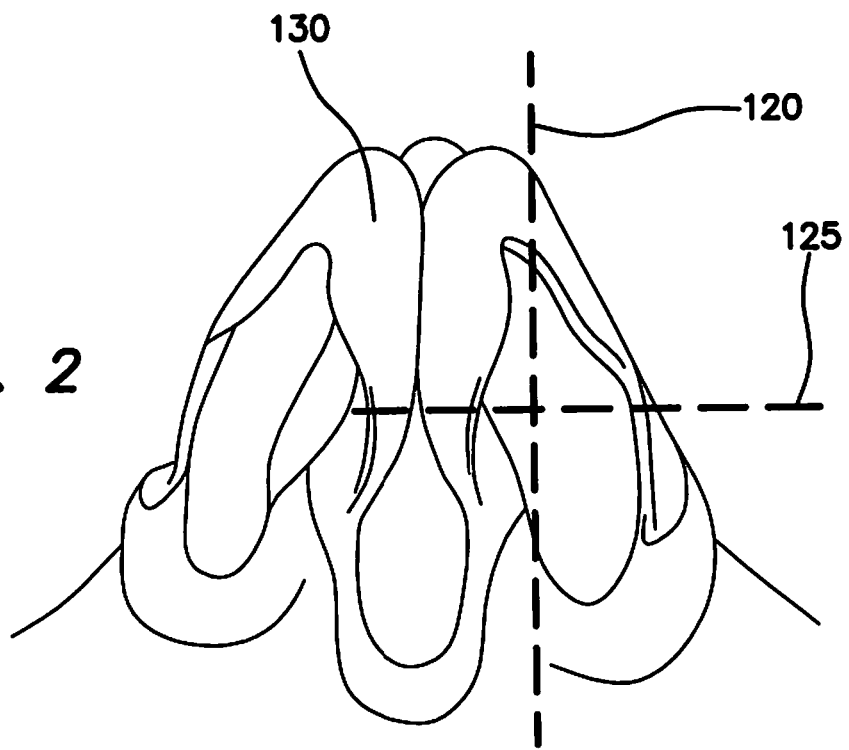
FIG. 2 illustrates an underside or base view of the anatomy associated with the human nose.

FIGS. 1-2 show the internal structure of the nose area. In general, the nose area consists of a nasal bone 105 and a lower cartilaginous area 110. The nasal bone 105 is covered by a single nasal muscle laterally positioned and minimal soft fatty tissue under the skin resulting in skin that is substantially fixed. The lower cartilaginous area 110 is comprised of multiple pieces of cartilage held together by connective tissue 115. The objective of the splint(s) of the present invention is to reduce the size of the connective tissue between the nasal cartilages 110 thereby enlarging (in a manner akin to a diaphragm) the vertical and horizontal diameters 120, 125, respectively, of the nostrils or lumens as identified by the dotted lines in FIG. 2. The nose columella 130 is also shown in FIG. 2

The most common cause of nasal valve obstruction relate to rhinoplasty, nasal trauma, and congenital anomalies.

Now referring to FIGS. 3*a*-5*b*, a vertical nasal splint 200 extends from an upper portion 205 of the nose near the nasal bone 105 to a lower level 210 of the nose near the columella 130. In this manner, the vertical splint 200 elevates the nasal columella 130 (from the base) and the nasal tip. Such a configuration assists patients with high noses, collapsed nasal tips common in Caucasian adults and/or congenital abnormalities.

Figure 6:
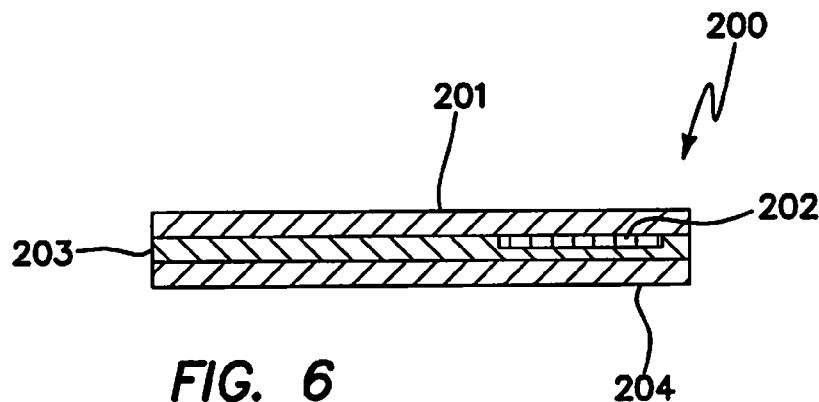
FIG. 6 shows a cross-sectional view of a vertical splint according to the embodiments of the present invention.

In one embodiment, the vertical splint 200 is fabricated of a hypoallergenic adhesive tape surrounding a plastic or combination of silicone and plastic (known as Silastic®) forming a flexible section. Those skilled in the art will recognize that other flexible materials may be used as well. In one exemplary version, the vertical splint 200 comprises three layers. In one exemplary version, as shown in FIG. 6 detailing a cross-sectional view along the length of the vertical splint 200, an outermost layer 201 comprises waterproof pliable material such as plastic, vinyl, latex rubber or the like. A second intermediate layer comprises a more rigid flexible section 202 made of rigid plastic, Silastic® or the like forming the flexible section. In one embodiment, the flexible section is ½ inch by ⅛ inch. However, the flexible section may be larger or smaller as needed. The flexible section is positioned near a portion of the vertical splint 200 intended to extend over the tip of a wearer's nose at the level of the columella 130. A third layer 203 is an adhesive layer comprising a non-allergenic glue. The vertical splint 200 may be packaged with a fourth layer comprising wax-paper 204 or similar non-stick materials positioned over the adhesive layer 203 to protect the same until application.

As shown, the vertical splint 200 is I-shaped to maintain the vertical splint 200 in place. The I-shaped vertical splint 200 can be made of three individual members comprising two horizontal members 205 and a single vertical member 206 extending therebetween, or a single member with an I-shape configuration. It is conceivable that the vertical splint 200 may take on other shapes. In one embodiment, the vertical portion of the vertical splint 200 measures approximately 2 inches in length by ¼ inch in width. In an alternative embodiment, the vertical portion of the vertical splint 200 measures 3 inches in length by ¼ inch in width. The vertical splint 200 may take on other dimensions to accommodate other nose sizes.

Application of the vertical splint 200 comprises: 1) removal of the wax-paper adhesive protective layer to expose the adhesive; 2) application of the end of the vertical splint 200 including the flexible section at the base of the columella; 3) extension of the vertical splint 200 up to the nasal tip 206; 4) elevation of the nasal tip 206 with a finger on a first hand; and 5) extension of the vertical splint 200 with a finger on a second hand onto the nasal bony area.

Figure 3A:
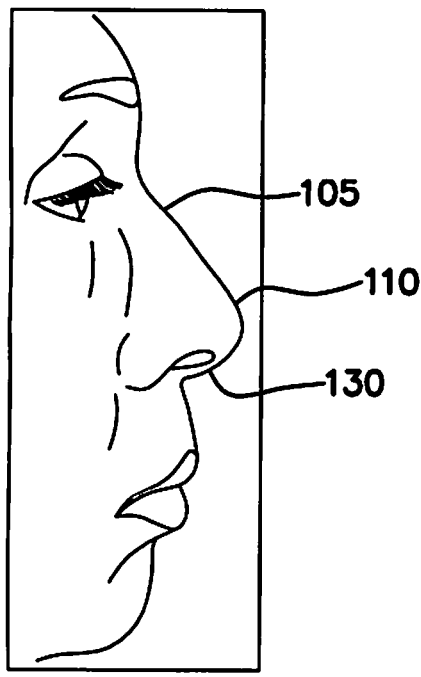
FIGS. 3*a* and 3*b* illustrate a front view of a vertical splint attached to a nose according to the embodiments of the present invention and the nose without the vertical splint, respectively.
Figure 3B:
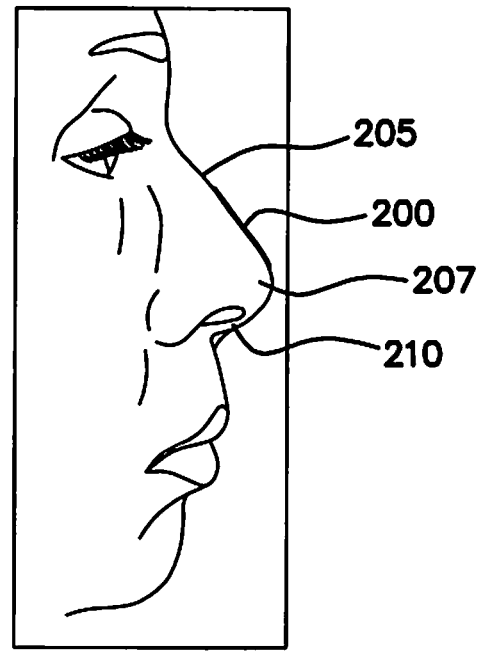
Figure 4A:
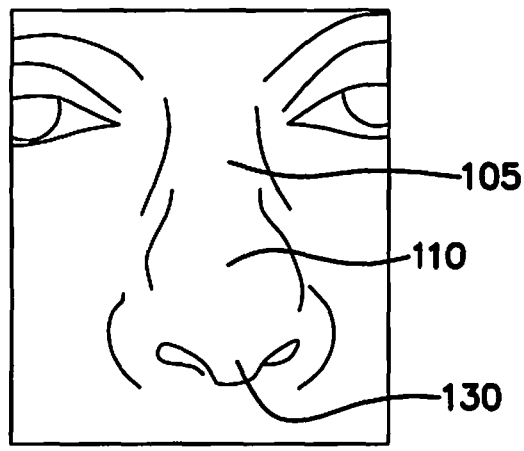
FIGS. 4*a* and 4*b* illustrate a side view of a vertical splint attached to a nose according to the embodiments of the present invention and the nose without the vertical splint in place, respectively.
Figure 4B:
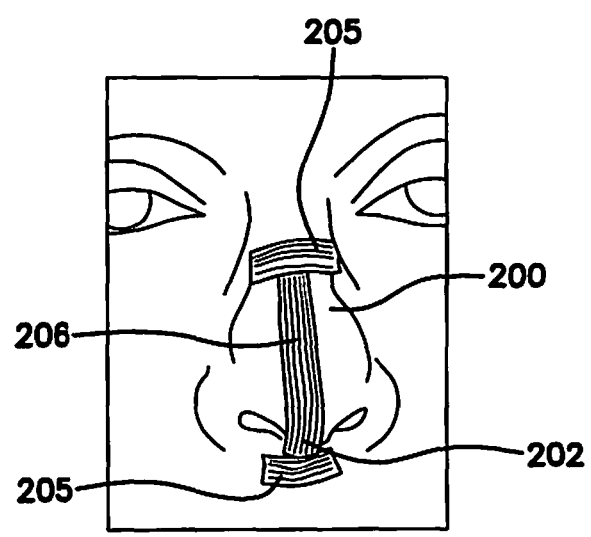
Figure 5A:
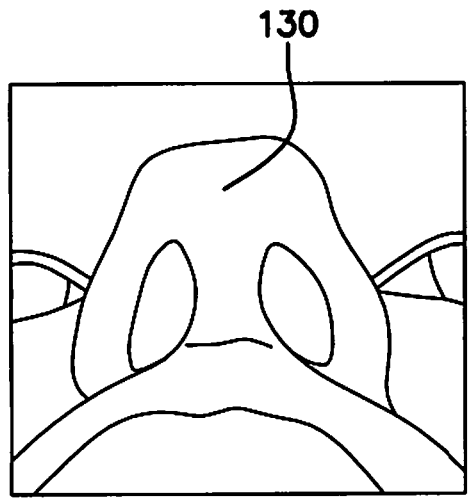
FIGS. 5*a* and 5*b* illustrate an underneath view of a vertical splint attached to a nose according to the embodiments of the present invention and the nose without the vertical splint in place, respectively.
Figure 5B:
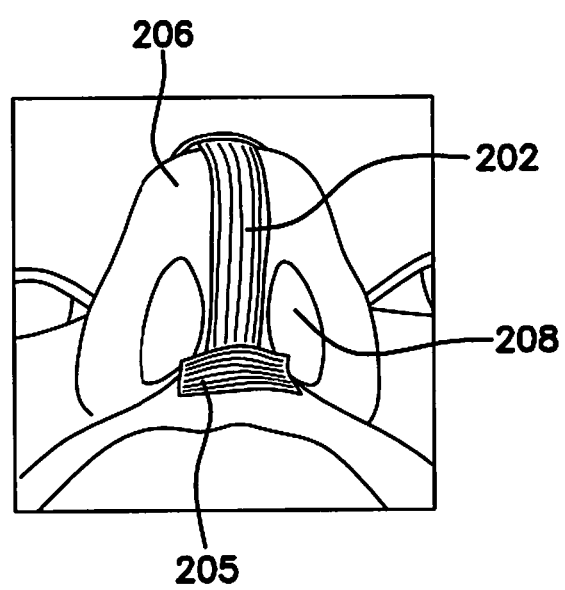

FIGS. 3b, 4b and 5b show the effect of the vertical splint 200 on the nose. FIGS. 3b and 4b show that the nasal tip 206 is elevated with the vertical splint 200 in place relative to the nose without the splint 200 in place as shown in FIGS. 3a and 4a. FIG. 5b shows the nostrils or lumens 208 expanded.

Now referring to FIGS. 7a-9 the horizontal splint 300 is configured to expand the connective tissue laterally and the external area of the nasal valves generally. In so doing, the horizontal diameter is increased preventing the collapse of nasal soft tissues during breathing.

Figure 7A:
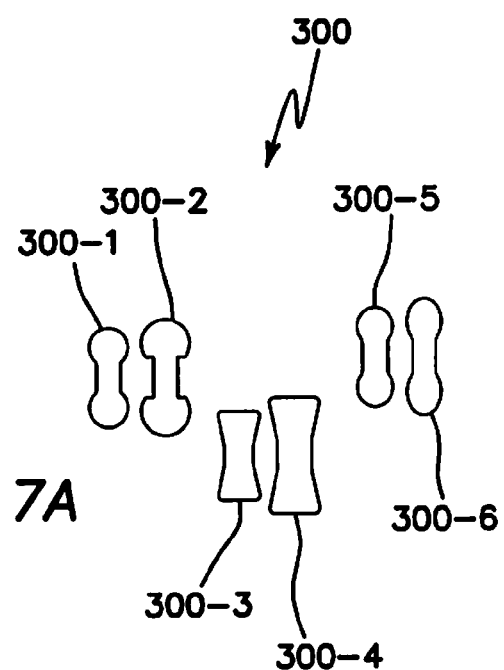
FIGS. 7*a* and 7*b* illustrate exemplary horizontal splint designs according to the embodiments of the present invention.
Figure 7B:
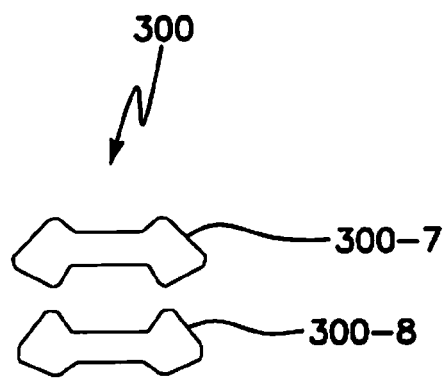

As shown in FIGS. 7a and 7b, the horizontal splint 300 may take on many shapes and dimensions. Horizontal splints 300-1 and 300-2 comprise tear drop configurations; horizontal splints 300-3 and 300-4 comprise quadrilateral configurations; horizontal splints 300-5 and 300-6 comprise circumferential configurations; and horizontal splints 300-7 and 300-8 comprise triangular configurations. The various configurations are designed pursuant to anatomy, histology and physiology of the nose to contact the weakest points on the lateral walls of the nose to prevent collapse of the nasal soft tissues during breathing. Simultaneously, the horizontal splints 300 attach to the nasal bone area to maintain resistance which also assists in preventing the collapse of the nasal tissues.

Figure 10:
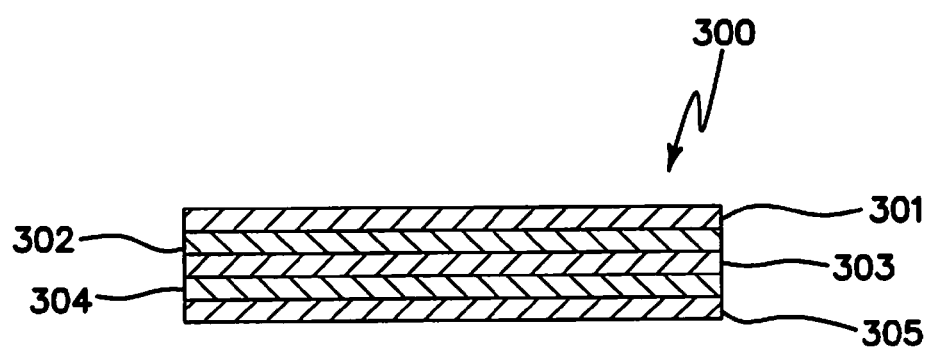
FIG. 10 illustrates a cross-sectional view of a horizontal splint according to the embodiments of the present invention.

The horizontal splint 300 may comprise four or five layers. As shown in FIG. 10 detailing a cross-sectional view along the length of the horizontal splint 300, an outermost layer 301 comprises waterproof pliable material such as plastic, vinyl, latex rubber or the like. An adjacent layer comprises a more rigid flexible section 302 made of rigid plastic, Silastic® or the like forming a flexible section acting as a spring. The flexible section 302 may or may not extend the length of the horizontal splint 300. That is, the flexible section 302 may only extend outward in both directions from a center portion to a point prior to the outer edges of the triangular portions. A third layer 303 comprises a non-allergenic clear glue. An optional fourth layer 304 comprises a porous membrane configured to absorb humidity. A fifth layer 305 (or fourth layer if the porous membrane is not used) comprises wax-paper or similar non-stick materials positioned over the adhesive layer 303 to protect the same until application.

Figure 8:
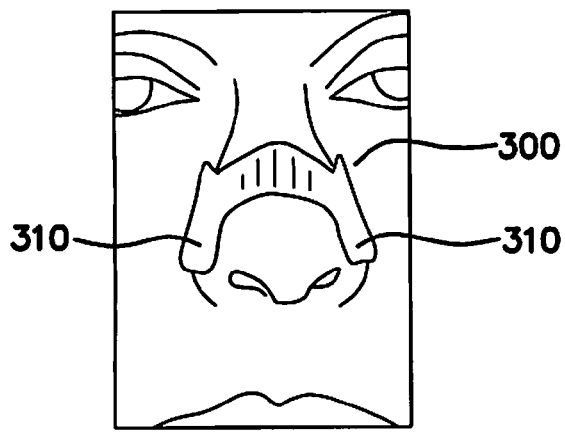
FIG. 8 illustrates a front view of a horizontal splint attached to a nose according to the embodiments of the present invention.
Figure 9:
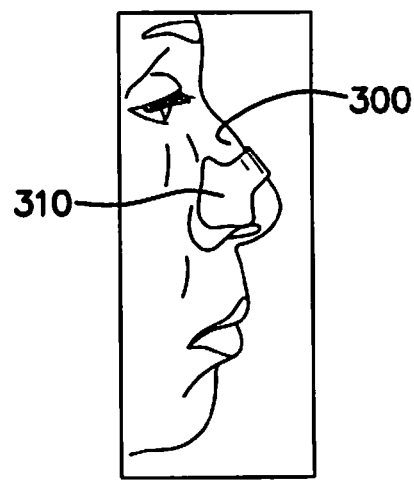
FIG. 9 illustrates a side view of a horizontal splint attached to a nose according to the embodiments of the present invention.

Application of the horizontal splint 300 comprises: 1) removal of the first section of the wax-paper to expose the hypoallergenic glue; 2) application of one triangular member with the base (wider portion) of the triangular portion facing inferiorly; 3) application of the apex of the triangular portion at the nasal bone 105 with the base of the triangular portion near the level of the nasal rim; and 4) removal of the second section to allow application of the second triangular portion to the opposite side of the nose. FIGS. 8 and 9 show the horizontal splints 300 having triangular regions 310 positioned on a nose.

Figure 11A:
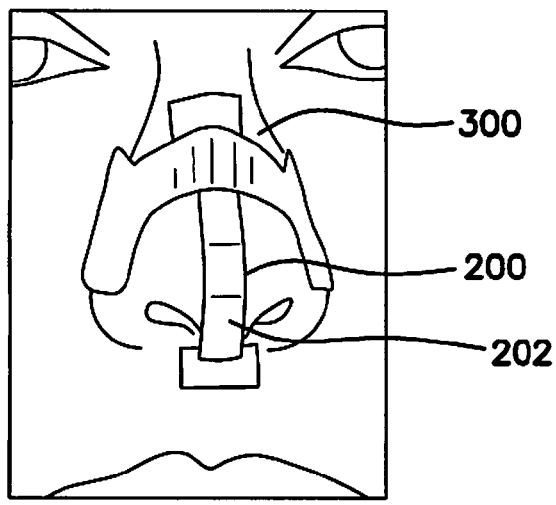
FIGS. 11*a* and 11*b* illustrate a front view and side view, respectively, of a vertical and horizontal splints attached to a nose according to the embodiments of the present invention.
Figure 11B:
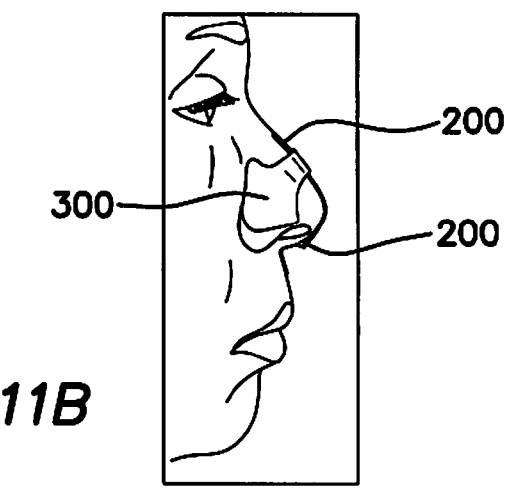
Figure 12:
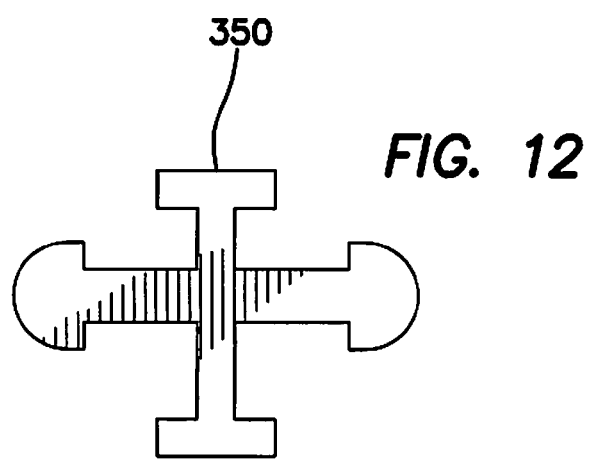
FIG. 12 illustrates a front view of a singular vertical/horizontal splint attached to a nose according to the embodiments of the present invention.

FIGS. 11a and 11b show the vertical splint 200 and horizontal splint 300 being worn by a user. As shown, the vertical splint 200 and horizontal splint 300 are individual, separate items. Alternatively, the vertical splint 200 and horizontal splint 300 may be a single unit 350 as shown in FIG. 12. The combination of the vertical splint 200 and horizontal splint 300 increases the vertical and horizontal diameters in the lumen of the lower portion of the nose thereby improving the flow of oxygen into the nose.

Although the invention has been described in detail with reference to several embodiments, additional variations and modifications exist within the scope and spirit of the invention as described and defined in the following claims.

I claim:

1. A nasal opening apparatus comprising:
a vertical splint configured to extend from an upper portion of a nose over the nose tip and to below the columella, a vertical splint flexible member integrated as part of said vertical splint and positioned such that upon attachment of the vertical splint to a nose the flexible member is adjacent to a nose tip and assists with maintaining a nose tip in an elevated position relative to a normal nose tip position, said vertical splint having an adhesive layer for attachment to a nose; and
a horizontal splint configured to extend from a first lateral wall to a second lateral wall of a nose, a horizontal splint flexible member integrated as part of said horizontal splint and extending from said first lateral wall to said second lateral wall of a nose, said horizontal splint having an adhesive layer for attachment to a nose.

2. The nasal opening apparatus of claim 1 wherein said vertical splint is I-shaped.

3. The nasal opening apparatus of claim 1 wherein said horizontal splint has ends shaped as a tear drop, quadrilateral, circle or triangle.

4. The nasal opening apparatus of claim 1 wherein said horizontal splint further includes a porous membrane configured to absorb humidity.

5. The nasal opening apparatus of claim 1 wherein said vertical and horizontal splints are independent and separate.

6. The nasal opening apparatus of claim 1 wherein said vertical and horizontal splints are a single unit.

7. A nasal opening apparatus comprising:

a vertical splint, including a vertical splint flexible member, dimensioned to extend from below the columella over the nose tip to an upper portion of the nose, said vertical splint, when attached to a nose, acts to elevate a nose tip relative to a normal nose tip position, said vertical splint flexible member integrated as part of said vertical splint such that the flexible member is positioned adjacent to a nose tip when said vertical splint is attached to a nose, said vertical splint having an adhesive surface for attachment to a nose; and a horizontal splint configured to extend from a first lateral wall to a second lateral wall of a nose, a horizontal splint flexible member integrated as part of said horizontal splint and extending from said first lateral wall to said second lateral wall of a nose, said horizontal splint having an adhesive surface for attachment to a nose.

8. The nasal opening apparatus of claim 7 wherein said vertical splint is I-shaped.

9. The nasal opening apparatus of claim 7 wherein said horizontal splint has ends shaped as a tear drop, quadrilateral, circle or triangle.

10. The nasal opening apparatus of claim 7 wherein said horizontal member further includes a porous membrane configured to absorb humidity.

11. The nasal opening apparatus of claim 7 wherein said vertical and horizontal splints are independent and separate.

12. The nasal opening apparatus of claim 7 wherein said vertical and horizontal splints are a single unit.

13. A nasal opening apparatus comprising:

a vertical splint having a first end for attachment to a nose proximate an upper portion of a nose, a body extending over a nose tip, and a second end for attachment to below the columella, a vertical splint flexible member integrated as part of said vertical splint and positioned such that upon attachment of the vertical splint to a nose the flexible member acts to maintain a nose tip in an elevated position relative to a normal nose tip position, said vertical splint having an adhesive layer for attachment to a nose; and a horizontal splint configured to extend from a first lateral wall to a second lateral wall of a nose, a horizontal splint flexible member integrated as part of said horizontal splint and extending from said first lateral wall to said second lateral wall of a nose, said horizontal splint having an adhesive layer for attachment to a nose.

14. The nasal opening apparatus of claim 13 wherein said vertical splint includes a horizontal member at one or both ends thereof.

15. The nasal opening apparatus of claim 1 wherein said vertical splint is configured to attach to the columella as the vertical splint extends from below the columella to the nose tip and upper portion of the nose.

16. The nasal opening apparatus of claim 7 wherein said vertical splint is configured to attach to the columella as the vertical splint extends from below the columella to the nose tip and upper portion of the nose.

17. The nasal opening apparatus of claim 13 wherein said vertical splint is configured to attach to the columella as the vertical splint extends from below the columella to the nose tip and upper portion of the nose.

* * * * *